US009689803B1

(12) United States Patent
Ruttner

(10) Patent No.: US 9,689,803 B1
(45) Date of Patent: Jun. 27, 2017

(54) METHOD AND SYSTEM FOR MEASURING A COLORIMETRIC CHARACTERISTIC OF A SAMPLE AND CALIBRATION OF SAME

(71) Applicant: Gabriel T. Ruttner, Roslyn Heights, NY (US)

(72) Inventor: Gabriel T. Ruttner, Roslyn Heights, NY (US)

(73) Assignee: Chroma Fish Corp., Roslyn Heights, NY (US)

( * ) Notice: Subject to any disclaimer, the term of this patent is extended or adjusted under 35 U.S.C. 154(b) by 0 days.

(21) Appl. No.: 15/133,652

(22) Filed: Apr. 20, 2016

(51) Int. Cl.
| | |
|---|---|
| G06K 9/00 | (2006.01) |
| G01N 21/80 | (2006.01) |
| G06K 9/46 | (2006.01) |
| G06K 9/62 | (2006.01) |
| G06T 7/40 | (2017.01) |
| H04N 1/32 | (2006.01) |
| H04N 1/46 | (2006.01) |
| G06T 7/00 | (2017.01) |
| G01J 3/52 | (2006.01) |

(Continued)

(52) U.S. Cl.
CPC ............... G01N 21/80 (2013.01); G01J 3/50 (2013.01); G01J 3/524 (2013.01); G01N 33/84 (2013.01); G06K 9/4652 (2013.01); G06K 9/6202 (2013.01); G06T 7/0085 (2013.01); G06T 7/408 (2013.01); H04N 1/3224 (2013.01); H04N 1/32133 (2013.01); H04N 1/46 (2013.01); G06T 2207/10024 (2013.01); G06T 2207/30204 (2013.01)

(58) Field of Classification Search
None
See application file for complete search history.

(56) References Cited

U.S. PATENT DOCUMENTS

| 4,682,895 A * | 7/1987 | Costello ............. G01N 21/7703 |
| | | 250/227.11 |
| 5,201,755 A * | 4/1993 | Klement .............. A61B 5/1459 |
| | | 600/526 |

(Continued)

OTHER PUBLICATIONS

Chen et al., "A Simple and Efficient Image Pre-processing for QR Decoder", 2nd International Conference on Electronic & Mechanical Engineering and Information Technology (EMEIT 2012).

(Continued)

*Primary Examiner* — Feng Niu
(74) *Attorney, Agent, or Firm* — Barkume & Associates, P.C.

(57) ABSTRACT

A chemical characteristic of a material is measured using a calibration unit and container for holding a sample of the material. The calibration unit has a front portion and an imaging background positioned behind the sample and viewable through the container and the sample of the material, wherein a portion of the sample of the material is positioned in front of the imaging background so as to form a sample imaging region. A calibration strip extends along the front portion, which includes a location marker and a plurality of calibration indicia of differing colors. A computing device captures an image of the calibration strip and the sample imaging region. A calibration step is performed using the calibration strip to generate a calibration model, which is applied to the sample color vector to generate a calibrated sample color vector.

47 Claims, 10 Drawing Sheets

(51) Int. Cl.
*G01J 3/50* (2006.01)
*G01N 33/84* (2006.01)

(56) References Cited

U.S. PATENT DOCUMENTS

| | | | |
|---|---|---|---|
| 5,583,666 A | 12/1996 | Ellson et al. | |
| 6,016,161 A | 1/2000 | Robinson | |
| 6,249,593 B1* | 6/2001 | Chu | G01N 21/8483 |
| | | | 382/128 |
| 8,848,988 B2* | 9/2014 | Plickert | G01N 21/8483 |
| | | | 382/128 |
| 8,877,140 B2* | 11/2014 | Chen | A61B 10/007 |
| | | | 422/400 |
| 8,911,679 B2* | 12/2014 | Chen | A61B 10/007 |
| | | | 422/400 |
| 9,129,350 B2* | 9/2015 | Setlur | G01N 21/8483 |
| 9,285,323 B2* | 3/2016 | Burg | G01N 21/78 |
| 9,311,520 B2* | 4/2016 | Burg | G01N 35/00029 |
| 9,445,749 B2* | 9/2016 | Erickson | G01N 33/52 |
| 9,528,941 B2* | 12/2016 | Burg | G01N 21/78 |
| 9,607,380 B2* | 3/2017 | Burg | A61B 5/1172 |
| 2006/0257285 A1 | 11/2006 | Burdon et al. | |
| 2007/0161103 A1* | 7/2007 | Buchmann | B26F 1/12 |
| | | | 435/287.2 |
| 2015/0055134 A1 | 2/2015 | Papautsky et al. | |
| 2015/0359458 A1 | 12/2015 | Erickson et al. | |
| 2016/0080548 A1* | 3/2016 | Erickson | H04M 1/72527 |
| | | | 455/556.1 |
| 2016/0266157 A1* | 9/2016 | Suzuki | G01N 33/491 |

OTHER PUBLICATIONS

Yetisen et al., "A Smartphone algorithm with inter-phone repeatability for the analysis of colorimetric tests," Sensors and Actuators B: Chemical, pp. 156-160, 2014, http://www.elsevier.com/locate/snb.

* cited by examiner

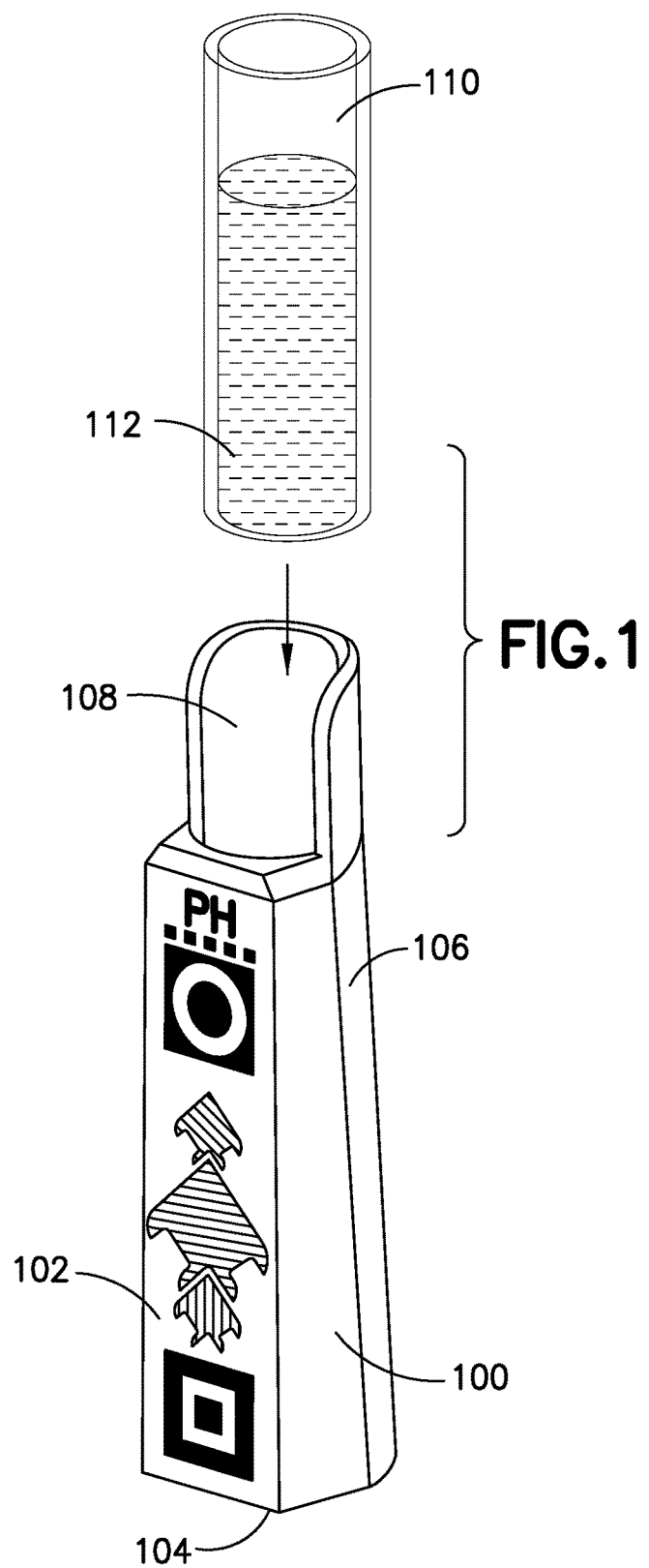

METHOD AND SYSTEM FOR MEASURING A COLORIMETRIC CHARACTERISTIC OF A SAMPLE AND CALIBRATION OF SAME

TECHNICAL FIELD

The method and apparatus disclosed and claimed herein relate to an improved manner of measuring a colorimetric chemical characteristic of a material, and in particular to measuring a colorimetric chemical characteristic of a sample of the material such as water from a fish tank or a pool using a computing device such as a smartphone that captures an image of the material sample and calibrates the colors in the sampled image to account for variations in lighting and the image sensor in the smartphone, and then calculates the chemical characteristic of the calibrated image for display to a user as well as further processing and analysis.

BACKGROUND

It is often required to measure one or more chemical characteristics of a sample of a material in order to ensure that the material complies with certain standards and take appropriate steps when the material is non-compliant. For example, it is desired to test the PH and other characteristics of water in a fish tank or pool, and then take corrective action if the PH is not within tolerance. Many types of chemistry test kits are available commercially that enable a user to test the water sample, such as test strips or mixing kits in which a reagent is added to the water sample that will turn the sample a certain color based on the PH of the water. Prior art test kits require a user to compare the color of the mixed water sample to a pre-printed chart by eye, which leads to errors in interpretation. Other prior art systems have been proposed in which a smartphone or other similar handheld computing device will capture an image of the water sample and then automatically compare the color(s) of the captured image to a predefined standard. Problems arise in this situation since the color(s) of the captured image will vary based on various parameters including but not limited to lighting conditions, optical qualities of the camera lens, and the sensitivity of the camera sensor. To attempt to compensate for these variations, calibration methodologies have been proposed whereby a calibration profile is pre-computed for a specific device and applied at the time of computation. This manual or infrequent calibration introduces measurement error as it is highly likely that the profile will change from the time of computation. Additionally, these proposed prior art methods are insufficient for various reasons, such as requiring the user hold the camera a fixed distance from the water sample. Other deficiencies in the prior art exist in the spatial region identification, wherein prior art methods do not clearly address finding the location of the sample in space which is required for future processing.

The method and apparatus disclosed and claimed herein overcome the deficiencies in the prior art for measuring a chemical characteristic of a material, and in particular in measuring a chemical characteristic of a sample of the material such as water from a fish tank or a pool, by using a computing device such as a smartphone that captures an image of the material sample and calibrates the image to account for variations in lighting and the image sensor in the smartphone, and then calculates the chemical characteristic of the calibrated image for display to a user as well as further processing and analysis.

SUMMARY

Thus, provided is a system and method for measuring a chemical characteristic of a material, for example measuring the PH of a sample of water obtained from a fish tank or a swimming pool. The present method utilizes a chemical measurement apparatus that includes the combination of a calibration unit and a container for holding the sample of the material being tested. For example, the container may be a transparent container such as a standard test tube that is provided with most commercially available fish tank water test kits, in which case the calibration unit and the test tube are provided as separate units, and the test tube is inserted into a channel in the calibration unit. Alternatively, the container and calibration unit may be provided as a single integrated unit. In either case, the calibration unit has a front portion and an imaging background that is positioned behind the sample of the material in the container and viewable through the container as well as the sample. As such, a portion of the sample of the material is positioned in front of the imaging background so as to form a sample imaging region. The imaging background provides a standard reference color to prevent colored light from the environment from changing the color of the imaging region. Additionally, the imaging background may block ballistic light from the environment to the sides of the sample. A calibration strip extends along the front portion of the calibration unit. The calibration strip includes a location marker and a plurality of calibration indicia that are each juxtaposed in relation to the location marker, wherein each of the plurality of calibration indicia is printed in a different color. For example, an RGB color space of red, green and blue may be used. The location marker includes any regions or marks which allow for spatial localization of the calibration unit. All other markers and imaging indicia are then located by some relation to the location marker.

After the sample of the material is placed into the container, a computing device such as a smartphone is used to capture an image of the calibration strip (the location marker and the plurality of calibration indicia) and the sample imaging region. Then, the smartphone executes a calibration step in order to adjust for variations in the captured image from what would otherwise be considered to be a true or standardized value (or calibrated color space), such as variations due to lighting as well as imperfections in the camera lens and/or sensor in the smartphone. The calibration step is performed by first analyzing the captured image to determine the location of the location marker within the image. This will provide a spatial reference which is used to calculate the location within the image of each of the plurality of calibration indicia. Next, a non-standardized (i.e. raw or uncalibrated) color value is extracted from each of the plurality of the calibration indicia, and then each non-standardized color value is compared to a previously stored standardized color value for a corresponding indicia. The offset between the non-standardized (raw) color value and a standardized color value for each indicia is then used to compute a calibration model, which may for example be a table of RGB values or a mathematical algorithm (e.g. regression). Thus, this step maps the entire non-standardized color space to a calibrated color space.

The next step is to locate in the captured image the imaging region(s) relative to the location marker. The color information in the imaging region is then adjusted from a non-standardized color space to a calibrated color space by computation with the calibration model constructed in the prior step. A second mapping is then computed from the calibrated color space to a chemical characteristic value via a chemical characteristic model. This model may take the form of a pre-computed regression model or stored table values and may have been obtained through theory or empirical derivation. For example, once the calibrated sample color value is computed in a water PH test, that color value can be analyzed to determine the PH of the water, if that PH is within a certain range, etc.

In an exemplary embodiment, the location marker on the calibration strip may include a pair of location targets, i.e. a first location target and a second location target. In this embodiment, the plurality of calibration indicia are located in a region between the first location target and the second location target. Thus, as long as the location of the calibration indicia with respect to the location marker is known, then the processing software is able to determine where in the image the calibration indicia may be found once the location of the location marker is determined.

The location targets preferably are printed as a black target on a white background, so that appropriate techniques such as edge detection routines may be used to ascertain the location of the targets in the captured image. In this case, the color value(s) of the location targets may also be included in the set of non-standardized color values that are extracted from the calibration indicia. For example, when the calibration indicia include a green calibration indicia, a blue calibration indicia, and a red calibration indicia, the captured location target(s) and the background color would then contribute the color black and white respectively to that set, which further increases the accuracy of the calibration step.

Optionally, a coded region may be juxtaposed in relation to the location marker and captured in the image by the smartphone. The coded region may be encoded with a printer identification and/or a chemical identification. The printer identification will indicate which printer was used to print the calibration strip during the manufacturing phase of the calibration unit, and will assist the calibration step in accounting for variations that may have existed during that printing step. The chemical identification will act to inform the processing software which chemical is being measured (e.g. PH), so that the appropriate chemical characteristic model may be used in the measurement step. Thus, when the coded region is implemented, the location of the coded region within the image is calculated by referencing the location of the location marker (in the same manner as calculating the location of the calibration indicia). The coded region is then decoded to provide the printer identification and/or the chemical identification. When the printer identification is decoded, then a printer calibration model associated with the printer identification is retrieved (e.g. from local memory or a resource located externally on the internet), and the calibration model is adjusted as a function of the printer calibration model. When the chemical identification is decoded, then that is used to retrieve the appropriate chemical characteristic model. In the event that the chemical identification is not encoded into the coded region, then the user would manually input the chemical identification into the smartphone such as by selection from a menu on the display, etc.

The coded region may be located on the calibration strip near the location marker and/or the calibration indicia. In an alternative embodiment, a cap may be provided that is suitable to cover the test tube container, and the coded region may be put on the cap such that the image will include the cap. This will allow the use of a single calibration unit and a different cap for each chemical that is being measured. In the embodiment using a cap, one of the location targets may also be located on the cap.

In an optional embodiment, the sample imaging background is not required. In this embodiment, a chemical measurement apparatus has a calibration unit with a calibration strip extending along a front portion of the calibration unit. The calibration strip includes a location marker and a plurality of calibration indicia juxtaposed in relation to the location marker, wherein each of the plurality of calibration indicia has a different color. A sample of the material is placed in close proximity to the calibration strip so as to form a sample imaging region. A computing device captures an image including the location marker, the plurality of calibration indicia, and the sample imaging region. The calibration steps are then performed, including analyzing the image to determine the location of the location marker within the image; calculating, by referencing the location of the location marker, the location within the image of each of the plurality of calibration indicia; extracting a non-standardized color value from each of the plurality of the calibration indicia; comparing the extracted non-standardized color values to a previously stored color standard; and generating a calibration model as a function of comparing the extracted non-standardized color values to the previously stored color standard. Next, the sample imaging region is analyzed from the image to extract a sample color vector (which may include or or more sample color values), and the calibration model is applied to the sample color vector to generate a calibrated sample color vector. Finally, the calibrated sample color vector is analyzed with respect to a chemical characteristic model in order to determine the measurement of the chemical characteristic of the material.

BRIEF DESCRIPTION OF THE DRAWING

FIG. 1 is a perspective view showing a calibration unit and container in a first embodiment in which the calibration unit is used as a base.

DETAILED DESCRIPTION OF THE PREFERRED EMBODIMENT

Figures 2A, 2B:
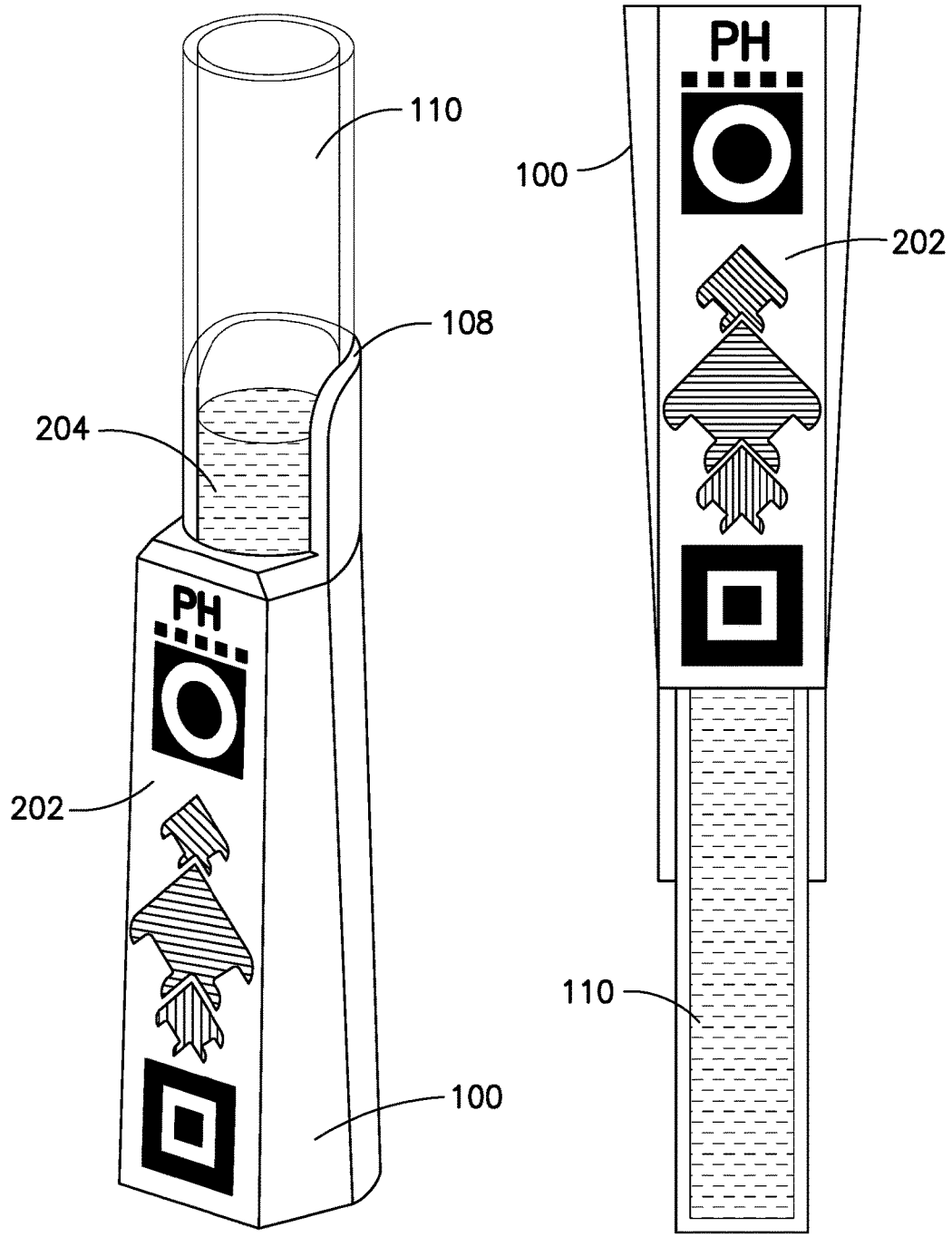
FIG. 2a is a perspective view showing the combination calibration unit and container of the first embodiment of FIG. 1.
FIG. 2b is a perspective view showing the combination calibration unit and container in a second embodiment in which the calibration unit is used as a cap for the container.

Referring to FIG. 1, a perspective view illustrates a calibration unit 100 and container 110 used in the method and apparatus described and claimed herein. The container 110 is shown as a transparent test tube that is commercially available, but any type of container may suffice as long as it mates with the calibration unit 100. The calibration unit 100 includes a base 104 for placing the calibration unit on a work surface such as a table. A front portion 102 that is substantially flat extends along the calibration unit 100 as shown, and a rear portion 106 extends further up the calibration unit 100 to provide an imaging background 108. The imaging background provides a standard reference color (e.g. white) to prevent colored light from the environment from changing the color of the imaging region. Additionally, the imaging background may block ballistic light from the environment to the sides of the sample.

In the illustrated embodiment, a channel is formed by the front portion 102 and the rear portion 106 so that the container (test tube) 110 may be placed therein as shown by the arrow. A sample 112 of the material being tested, in this case water from a fish tank, is poured into the container 110 so that the assembled device appears as in FIG. 2a. The exact amount of the sample 112 placed into the container is not critical, as long as enough is shown through the container so as to form a sample imaging region 204 that may be subsequently imaged.

A calibration strip 202 extends along the front portion 102 of the calibration unit 100. As shown in further detail in FIG. 6, the calibration strip 202 includes a first location target 604 and a second location target 606, which may be referred to collectively as a location marker. A plurality of calibration indicia 618, which in this embodiment are a first (green) calibration indicia 612, a second (blue) calibration indicia 614, and a third (red) calibration indicia 616, are juxtaposed in a region between the first location target 604 and the second location target 606. The shapes of the calibration indicia are shown as stylized fish since this example uses water from a fish tank; however, other shapes may be used if desired such as bars, circles, etc. As explained further herein, the exact locations of the first and second location targets and the calibration indicia 612, 614, 616 are not critical, as long as the processing software is able to detect the location targets and then calculate the locations of the calibration indicia based on a preprogrammed device model. That is, as long as the location of the calibration indicia 612, 614, 616 with respect to the location marker (targets 604 and 606) is known, then the processing software is able to determine where in the image the calibration indicia may be found once the location of the location marker is determined.

The location targets 604, 606 preferably are printed as a black target on a white background, so that proper edge detection routines may be used to ascertain the location of the targets in the captured image. If desired, the color value(s) of the location targets 604, 606 may also be included in the set of non-standardized color values that are extracted from the calibration indicia 612, 614, 616. Thus, in this embodiment, the captured location targets 604, 606 would then contribute the colors black and white to the set of calibration indicia that include the colors red, green and blue, which further increases the accuracy of the calibration step. Of course, other color spaces may be used if desired.

The calibration strip 202 may be a label that is printed and affixed onto the front portion 102 of the calibration unit 100 during a manufacturing process, as well known in the art. In the alternative, the location targets and calibration indicia may be printed directly onto the front portion 102 without using a separate label or other substrate, if desired.

Figure 6:
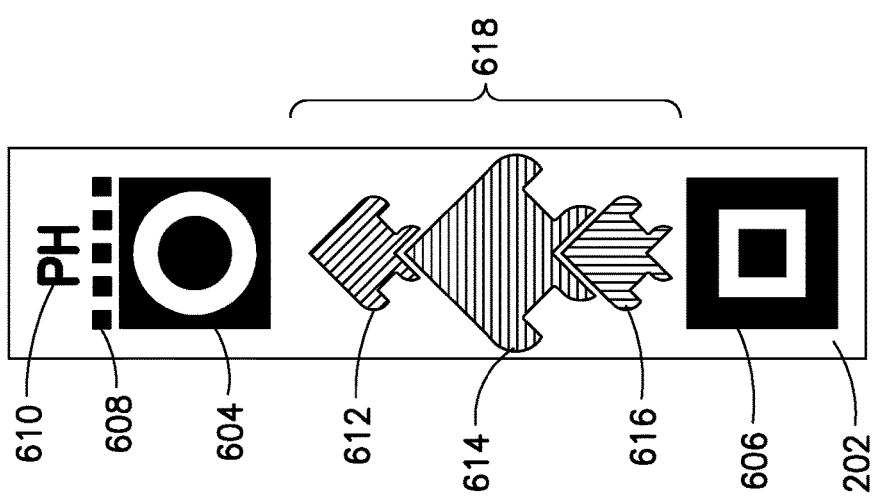
FIG. 6 illustrates an exemplary calibration strip.
Figure 8:
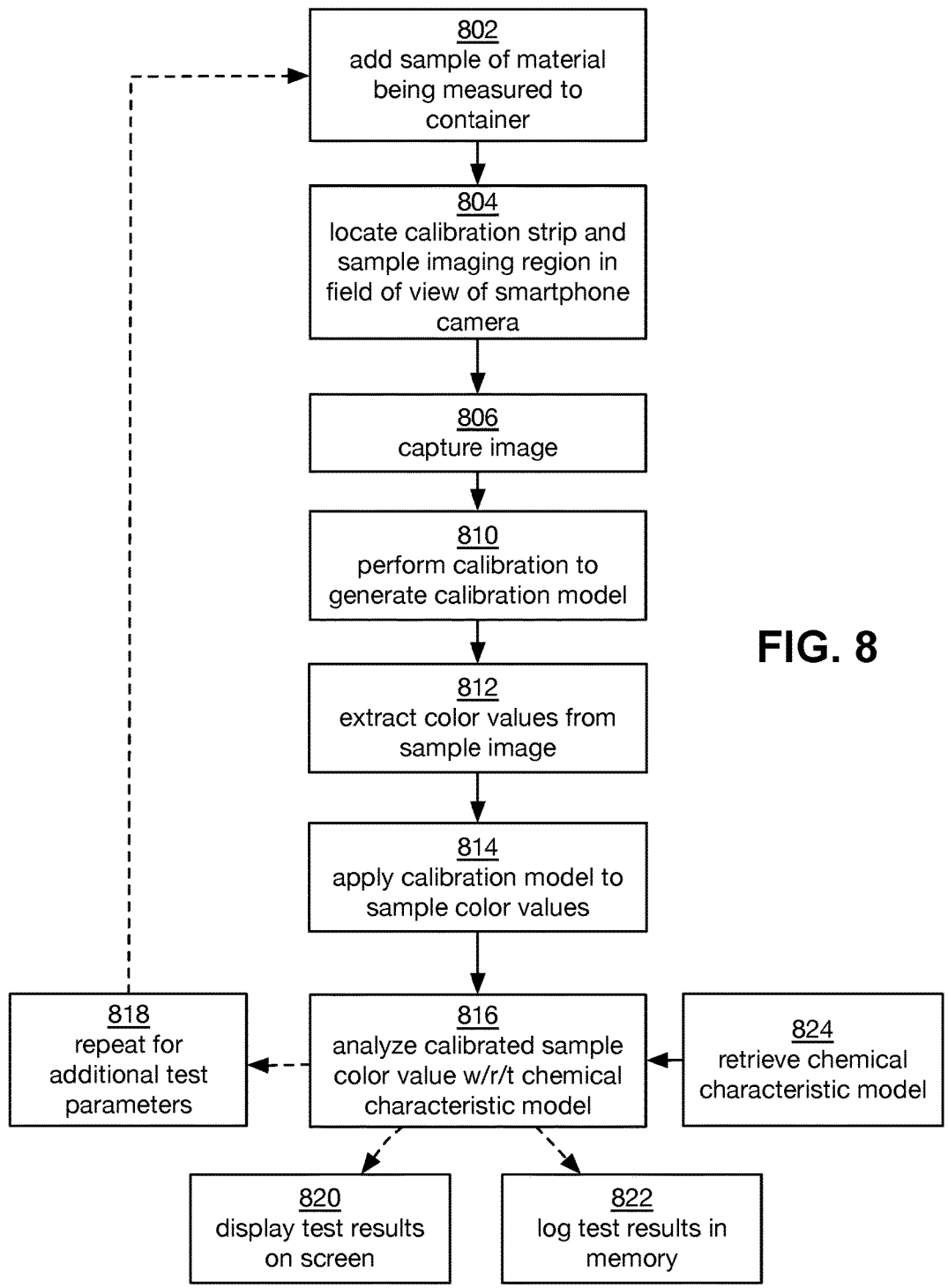
FIG. 8 is a flowchart of the overall functionality of the methodology disclosed and claimed herein.

Also shown in FIG. 6 is an optional coded region that includes a code 608 printed on the calibration strip 202. The code 608 is juxtaposed in relation to the location marker and will be captured in the image by the smartphone. The code 608 may be encoded with a printer identification that indicates which particular printer was used to print the calibration strip 202 during the manufacturing phase of the calibration unit 100. Because variations in color may exist in using different printers, it may be necessary to adjust the final calibrated image for those printer variations so that the analysis is accurate. The identification of the printer may thus be encoded and printed into the code 608. Code 608 may for example be a bar code, and once detected by the processing routines will provide a means for obtaining a printer calibration model from memory that is associated with that printer. For example, it may be known that printer #4 in the production line will oversaturate the color red, and then the printer calibration model associated with printer #4 will compensate for that oversaturation, leading to a more accurate calibration. An additional example would be a change in ink supplier on a certain date, at which point all printer identifications would be changed and new models deployed.

The coded region on calibration strip 202 may also include a text area 610 that indicates the identification of the chemical or property/parameter that is being tested. Thus, as shown in FIG. 6, the PH parameter is being tested by this particular embodiment. The PH text area 610 will enable the user of the apparatus to manually enter into the smartphone the selection of a PH test, for example from a menu listing of available tests, as described further herein. This chemical identification will act to inform the processing software which chemical property is being measured (PH), so that the appropriate chemical characteristic model may be used in the measurement step as described further below.

Additionally, the chemical identification may be encoded into the code 608 in addition to being printed in the text area 610. In this embodiment, the code 608 is located within the image and decoded to provide the chemical identification, instead of requiring the user to manually input the chemical identification as described above.

Thus, when this coded region is implemented, the location of the code 608 in the coded region within the image is calculated by referencing the location of the location marker (in the same manner as calculating the location of the calibration indicia). The code 608 is then decoded to provide the printer identification and/or the chemical identification. When the printer identification is decoded, then a printer calibration model associated with the printer identification is retrieved, and the calibration model is adjusted as a function of the printer calibration model. When the chemical identification is decoded, then that is used to retrieve the appropriate chemical characteristic model instead of requiring the user to manually input the chemical identification.

Figure 7:
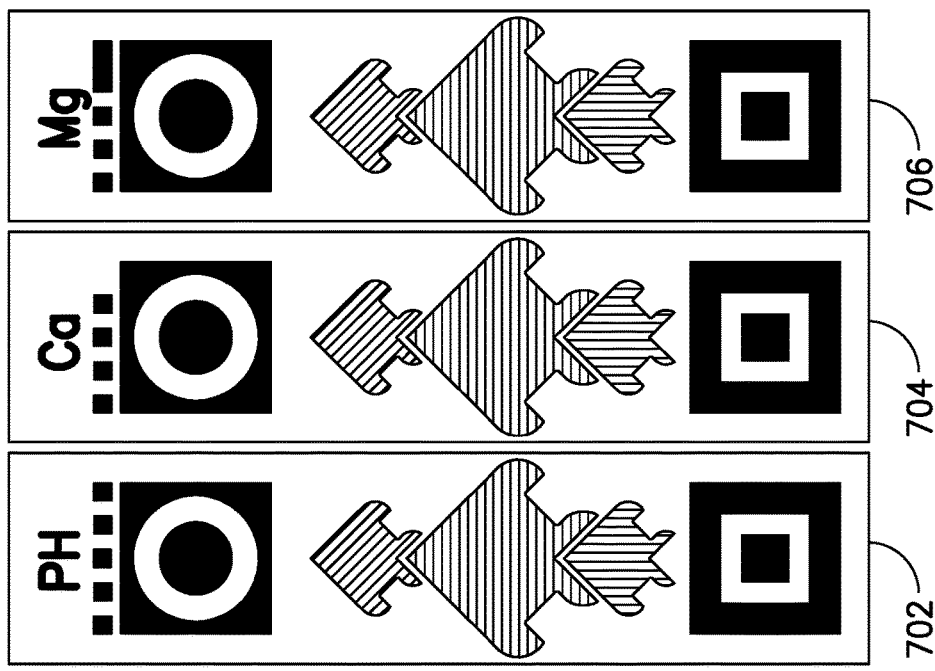
FIG. 7 illustrates three different calibration strips.

Of course, virtually any type of chemical characteristic may be measured as described herein, as may be desired. By way of a non-limiting example, FIG. 7 illustrates three different calibration strips 702, 704 and 706. As can be seen, each strip has a different code that corresponds to a different chemical being measured (PH, calcium, and magnesium), although the location targets and calibration indicia are the same as each other.

Figure 3:
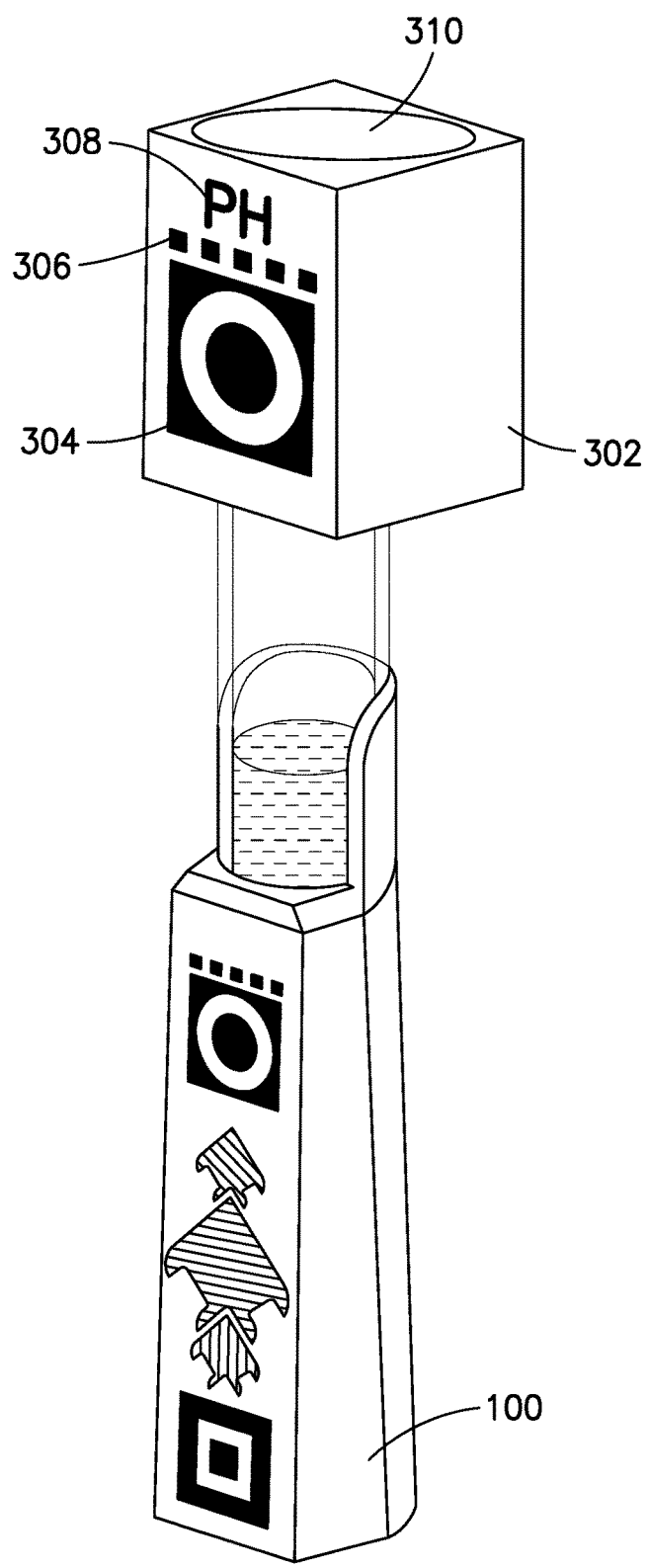
FIG. 3 is a perspective view showing the container inserted into the calibration unit in a third embodiment in which the calibration unit is used as a base and a calibration cap is placed on the container.

In an alternative embodiment as shown in FIG. 3, a calibration cap 302 is placed on the container 110. The calibration cap 302 is suitable to cover the test tube container 110, and the coded region may be put on the cap as shown. The calibration cap 302 in this example includes an auxiliary location target 304, an auxiliary code 306, and an auxiliary text area 308. The auxiliary location target 304 may be used in addition to the first location target 604 and the second location target 606, or it may be used in place of either one of them. That is, the location marker may include any subset or combination of all three location markers 604, 606, 304 as desired. The auxiliary location code may be used instead of the code 608 and function in the same manner, and the auxiliary text area 308 may be used instead of the text area 610 and function in the same manner as well. When the calibration cap 302 is implemented, the scanned image will include the cap and will allow the use of a single calibration unit 100 with a different cap for each chemical that is being measured.

Also shown in FIG. 3 is an optional recess 310, which may be provided to hold a vial of reagent, and thus enable a different cap to be used for a specific vial of reagent. This would allow the user to use the cap of the specific reagent they are using to hold the associated vial of reagent and keep the materials organized on a shelf or other storage area when not in use.

In addition to the primary embodiment in which the calibration unit 100 is used as a base into which the container is inserted as shown in FIG. 2a, the calibration unit may in the alternative be used as a cap that is placed over the test tube container 110 as shown in FIG. 2b. In this embodiment, the calibration strip 202 will likely be affixed to the calibration unit 100 so that it may be viewed by the user in the appropriate manner, although the smartphone may image the calibration strip 102 regardless of its orientation.

Figure 4:
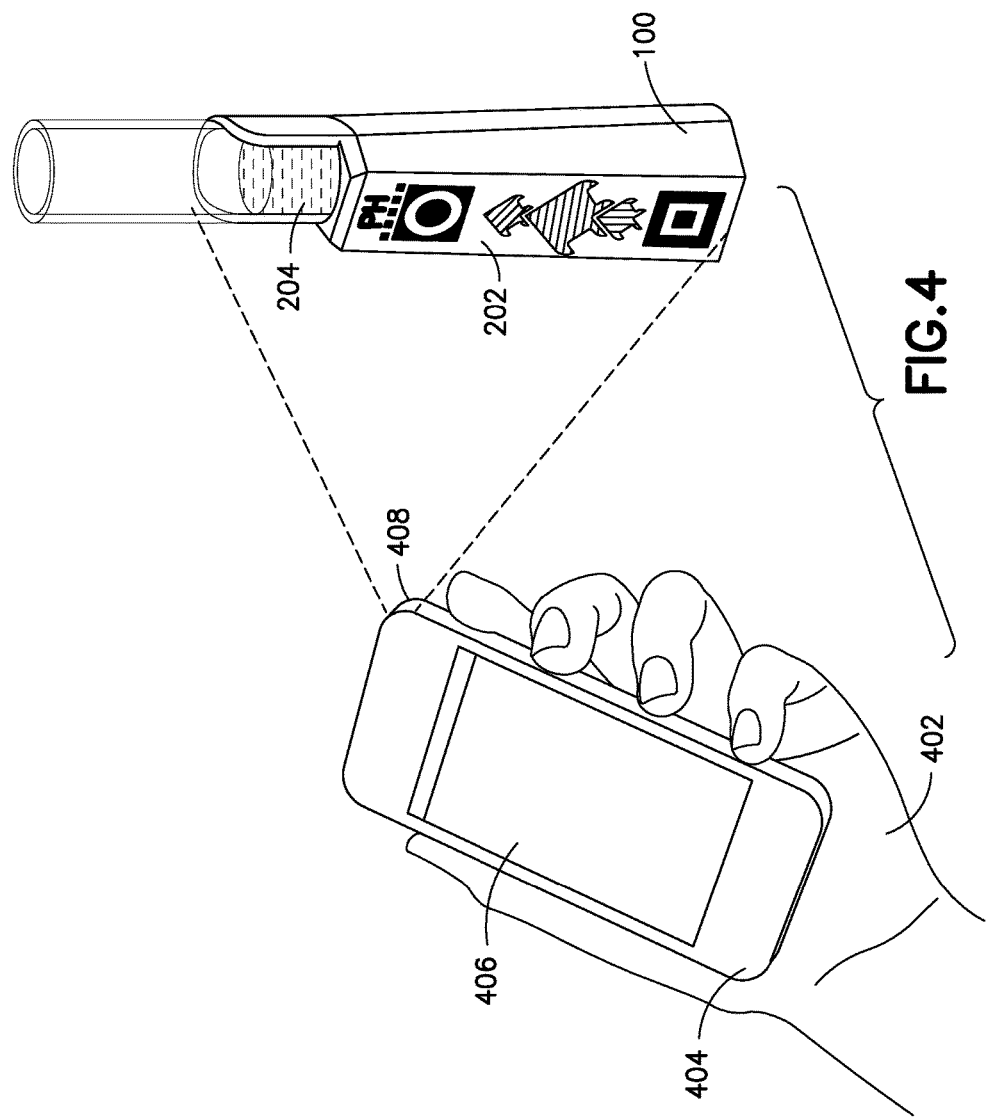
FIG. 4 illustrates a smartphone that is capturing an image of the combination calibration unit and container of the first embodiment.

FIG. 4 illustrates a smartphone 404 that is capturing with its camera 408 an image of the combination calibration unit and container of the first embodiment. The smartphone 404 is well known in the art, and may be an IPHONE, ANDROID phone, WINDOWS phone, etc. The user 402 will hold the smartphone 404 so as to capture an image 406 of the combination calibration unit 100 and container 110 of the first embodiment, and will be able to see the image 406 about to be captured in the display screen of the smartphone to ensure that it is captured properly.

Figure 5:
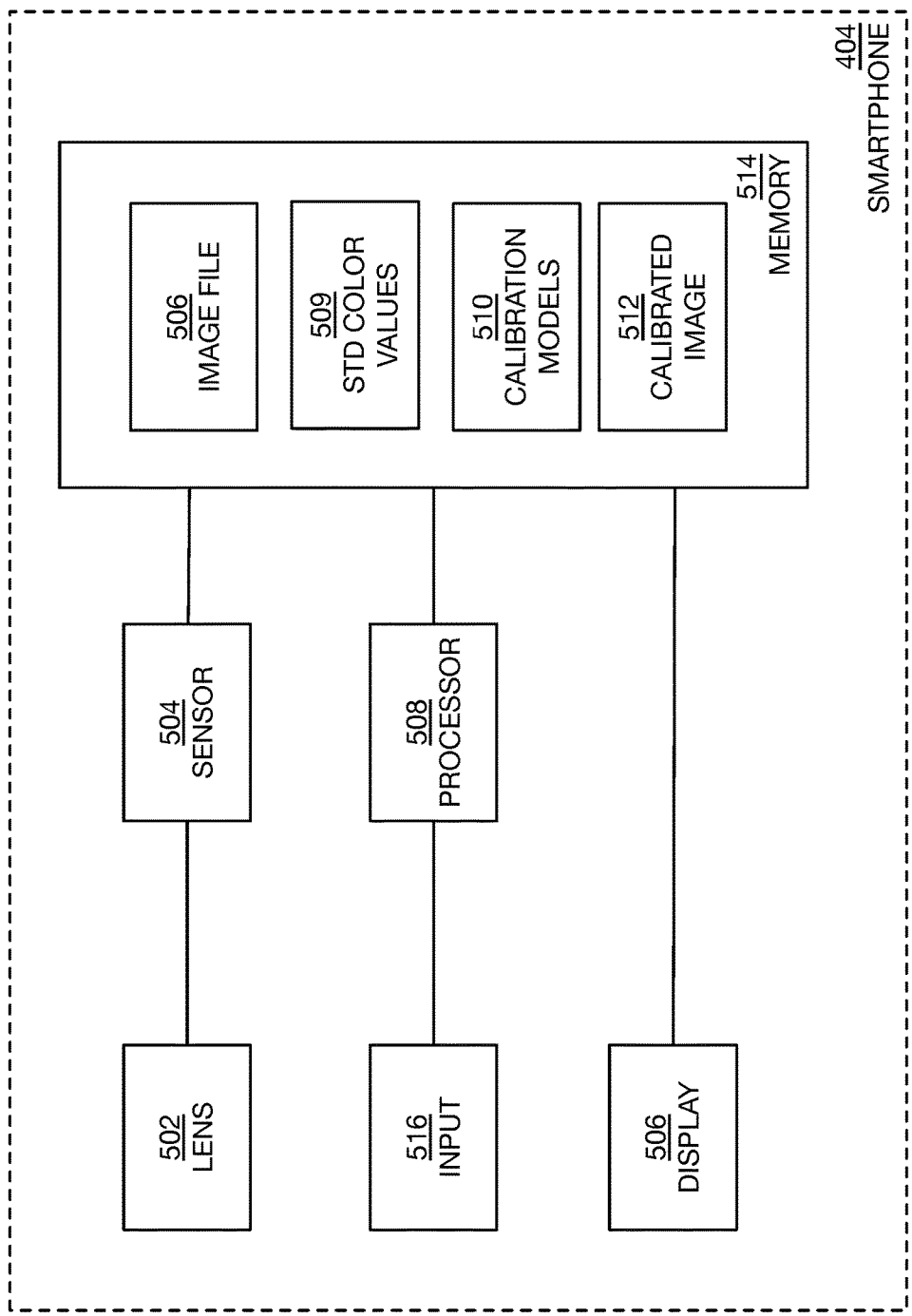
FIG. 5 is a block diagram of the functionality of the smartphone computing device.

The main components of the smartphone 404 that are utilized in this embodiment are shown in FIG. 5, and include a lens 502 and sensor 504 that in combination are also referred to as the camera 408, a processor 508, and memory 514. The memory 514 stores programming instructions as well known in the art to execute the processes described herein, and operating systems and other system files as known in the art. The memory will also store an image file 506 that is captured by the camera and obtained from the sensor 504, a set of standardized color values 509, calibration models 510 generated by the calibration step, and a calibrated image 512 that is obtained as a result of processing the image file 596 with the calibration models 510. Also shown are a display 506 which is typically a touchscreen display that enables the user to view the image 406 at the time of capture by the camera 408, as well as the results of the imaging and processing steps. The smartphone will also have one or more input devices 516, such as buttons, rocker switches and the like. In the embodiment in which the smartphone implements a touchscreen, then an input 516 and display 506 are implemented by the touchscreen as known in the art. As previously explained, any type of computing device in addition to a smartphone that provides the functionality described herein may be used with this system, including but not limited to tablets such as IPADS, an IPOD touch, etc.

With reference to the flowcharts of FIG. 8-11, the specific processing and operation will now be described. At step 802, a sample of the material being measured (for example, water taken from a fish tank) is added into the container 110. An amount of reagent may be added to the container and mixed with the sample as provided typically by instructions that accompany the reagent. As previously described, its is important to ensure that enough of the sample/reagent mixture is visible through the container 110 at the imaging background 108 so as to provide the sample imaging region 204 as shown in FIG. 2. At step 804, the user will locate the calibration strip 202 and sample imaging region 204 in the field of view of the smartphone camera. At step 806, the user will use the smartphone camera to capture an image 406 that includes the calibration strip 202 and the sample imaging region 204. Note that in the embodiment shown in FIG. 3, the image will also include the calibration cap 302.

Figure 9:
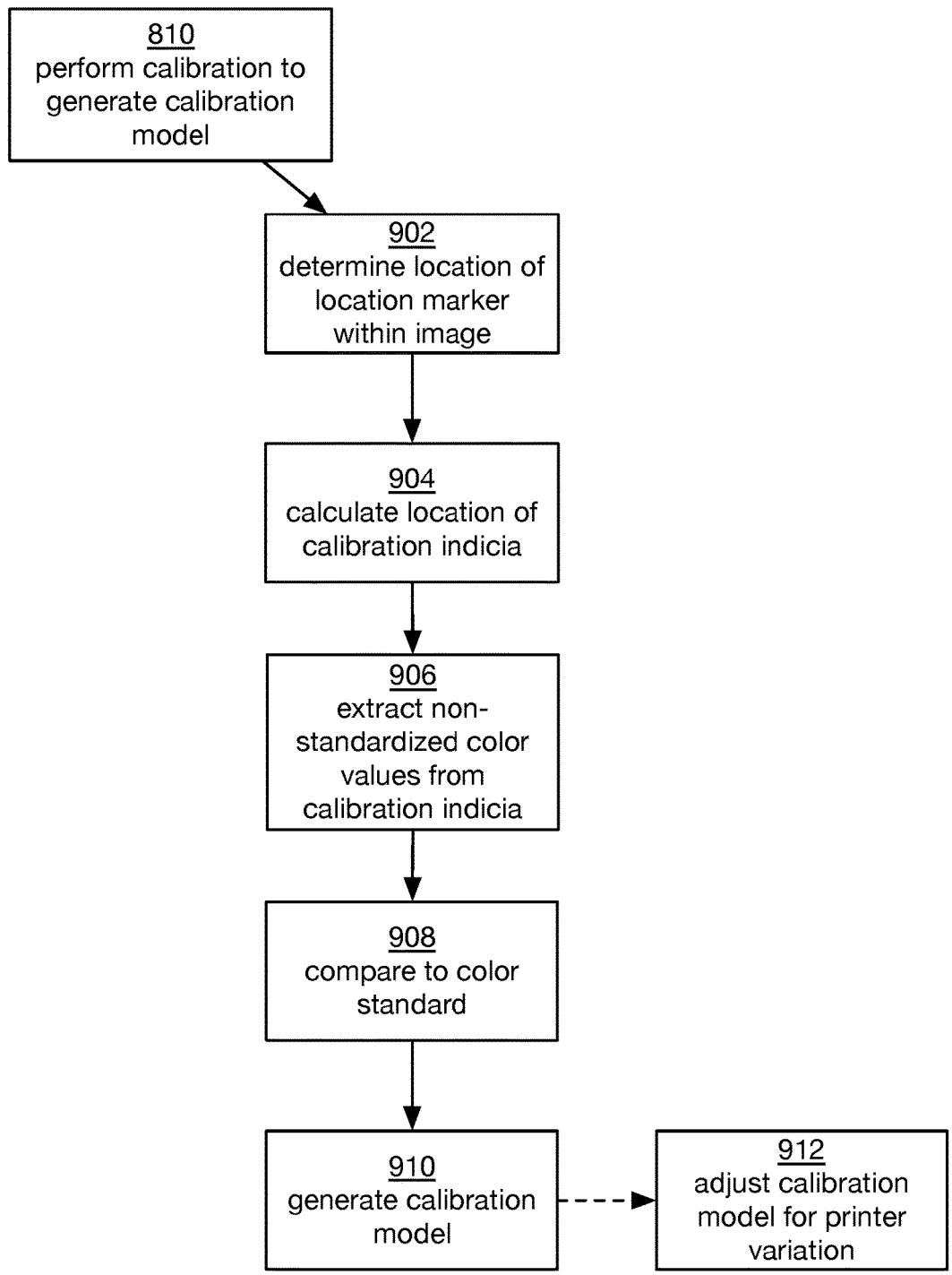
FIG. 9 is a flowchart of the calibration model generation of the methodology disclosed and claimed herein.

After the image 406 is captured by the smartphone, a calibration process is executed by the smartphone at step 810. With further reference to FIG. 9, the calibration process operates as follows. First, at step 902, the image file 506 is analyzed to determine the location of the location marker within the image. In the embodiment shown in FIG. 6, the location marker includes the first location target 604 and the second location target 606. These location targets are found by edge detection techniques or other sampling techniques as known in the art, such as those used by processing routines that analyze two-dimensional codes known as QR codes. For example, the reference A Simple and Efficient Image Pre-processing for QR Decoder, Chen et al., $2^{nd}$ International Conference on Electronic & Mechanical Engineering and Information Technology (EMEIT 2012), which is incorporated by reference herein, is illustrative of an exemplary technique, although others may of course be used.

Once the locations of the location targets are established, then the processing software is able to calculate the locations of the various calibration indicia at step 904. That is, the spatial relationship between the location targets 604, 606 and the calibration indicia 612, 614, 616 is stored in memory and used in this step. At step 906, a non-standardized color value is extracted for each of the calibration indicia 612, 614, 616 (e.g. green, blue and red). Then, at step 908, these extracted non-standardized color values are each compared to a previously-stored set of standardized color values. The offset between the non-standardized color taken from the imaged calibration indicia and a standardized value for each color is then used to compute a calibration model at step 910 (for example a table of RGB values or a mathematical algorithm (e.g. regression)). This step maps the entire non-standardized color space to a calibrated color space. The calibration model represents a shift of the non-standardized color values that will take place in order to adjust for the variations described above.

Referring back to FIG. 8, at step 812 the sample imaging region 204 is located within the image with respect to the previously found location targets 604, 606, and then a sample color vector, which may include one or more sample color values, is extracted from the sample imaging region. At step 814, the calibration model is applied to the sample color vector to generate a calibrated sample color vector. In this step, the actual color vector (values) of the sample is adjusted by the calibration model in order to compensate for the variations described above.

The specific processing algorithms implemented in executing the calibration and standardization routines are well known in the art and need not be repeated here. For example, reference is made to Yetisen et al., A Smartphone algorithm with inter-phone repeatability for the analysis of colorimetric tests, from Sensors and Actuators B: Chemical, pp 156-160, 2014, http://www.elsevier.com/locate/snb, which is incorporated by reference herein. Other algorithms for performing the calibration and standardization routines may also be used if desired.

Figure 11:
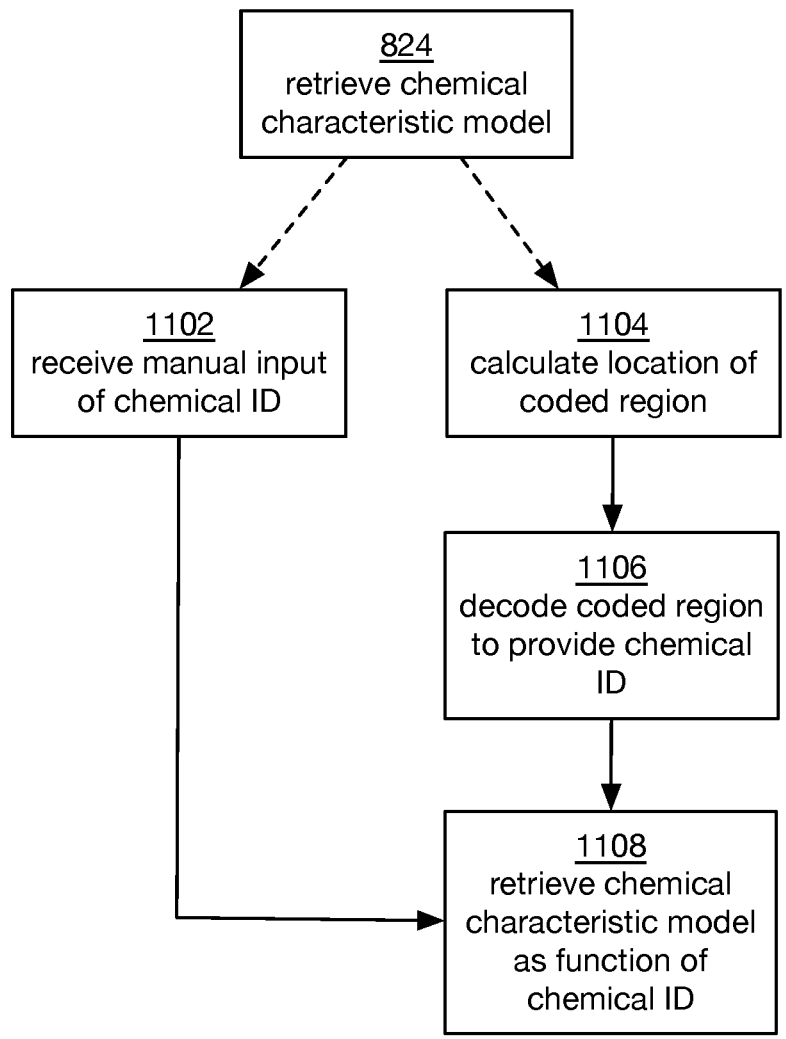
FIG. 11 is a flowchart of the manner of determining the chemical being measured by the method and apparatus described and claimed herein.

At step 824, a chemical characteristic model for the material being measured is retrieved from memory. For example, if PH is being tested, then the chemical characteristic model for PH is retrieved. With reference to FIG. 11, this may be done in one of at least two ways. In a simple embodiment, the user will make an entry into the smartphone by using an input such as the touchscreen at step 1102. For example, a menu listing may be displayed on the screen, which would list all of the possible chemical characteristics being measured, and the user would make a manual selection from the menu. Of course, a text entry may be provided, or a voice recognition routine may be employed (such as SIRI by APPLE) or any other manner for the user to enter manually the desired selection.

As explained above, the coded region on calibration strip 202 may also include a text area 610 that indicates the identification of the chemical characteristic that is being tested. As shown in FIG. 6, the PH parameter is being tested by this particular embodiment. The PH text area 610 will enable the user of the apparatus to manually enter into the smartphone the selection of a PH test.

In another embodiment, in order to avoid the manual entry of the characteristic identification, the chemical identification may be encoded into the code 608. In this embodiment, the code 608 is located within the image and decoded to provide the chemical identification, instead of requiring the user to manually input the chemical identification as described above.

Thus, when this coded region is implemented, at step 1104 the location of the code 608 in the coded region within the image is calculated by referencing the location of the location marker in the same manner as calculating the location of the calibration indicia. The code 608 is then decoded at step 1106 to provide the chemical identification, and at step 1108 the associated chemical characteristic model is retrieved from memory at step 1108 instead of requiring the user to manually input the chemical identification.

Once the chemical characteristic model has been retrieved from memory, the analysis of step 816 occurs. There, the calibrated sample color vector is analyzed with respect to the retrieved chemical characteristic model. For example, the analysis may determine that the calibrated color vector of the sample indicates that the PH of the sample is exceedingly low. At step 820 those analysis results may be displayed on the screen for the user to view. Optionally, at step 822, the analysis results may be stored in memory on the smartphone or transmitted wirelessly to an external store. The entire process may be repeated, for additional chemical characteristics other than PH, as shown at step 818.

Figure 10:
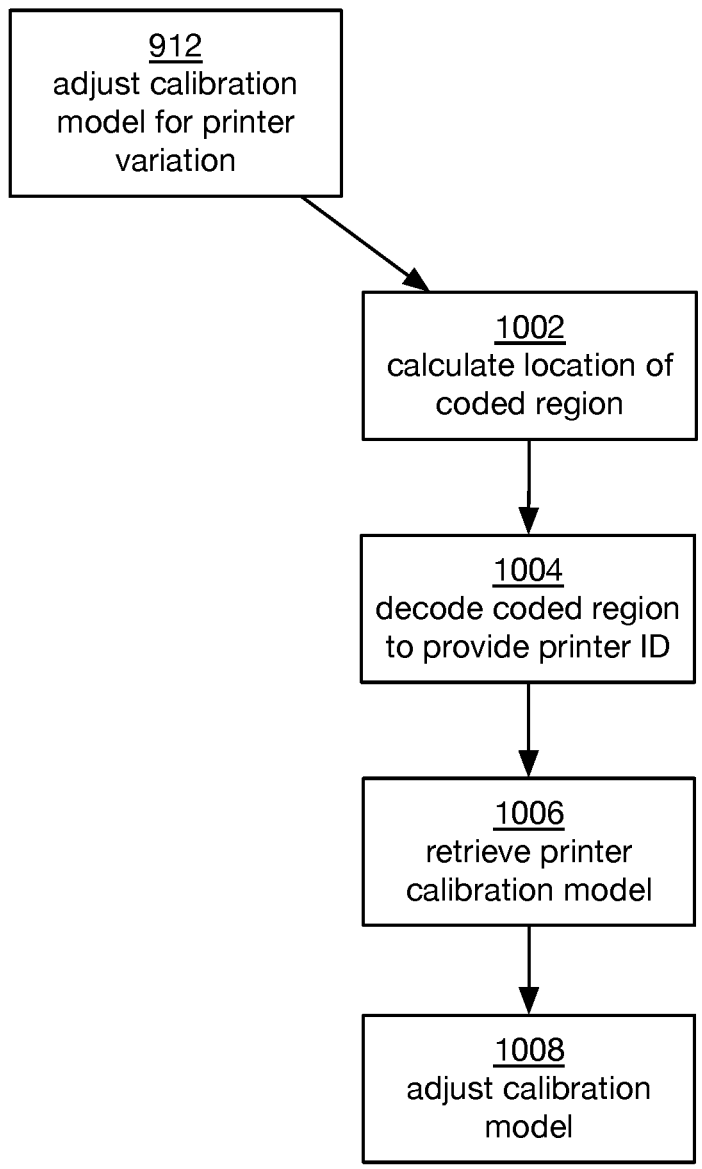
FIG. 10 is a flowchart of the printer calibration method disclosed and claimed herein.

FIG. 10 illustrates a flowchart of optional process steps that are executed in order to provide for calibration due to variations in the printing process of the calibration unit 100, in particular the various colors in the calibration strip 202. A printer calibration model may be stored locally in memory or on an external resource such as on the internet. The printer calibration model will provide an adjustment vector for the printer that was used to print the calibration indicia on the calibration strip 202. For example, a certain printer used in the manufacturing process of the calibration strip may print an oversaturated hue of blue, and that can be measured and adjusted for during the calibration process at step 912 of FIG. 9. The identification of the printer, and its associated printer calibration model, may be stored in the code 608, in addition to or instead of the chemical identification as described above. Thus, at step 1002 (see FIG. 10), the location of the code 608 in the coded region within the image is calculated by referencing the location of the location marker in the same manner as calculating the location of the calibration indicia. The code 608 is then decoded at step 1004 to provide the printer identification, and at step 1006 the associated printer calibration model is retrieved from memory. At step 1008, the calibration model may be adjusted in order to compensate for the variations in the printed calibration indicia.

Other features may be provided in alternate embodiments. For example, an illumination source, such as an LED light(s), may be integrated with the calibration unit 100 such that it provides illumination to the sample imaging region 204. Optionally, the imaging described above could then be done in a dark environment, so that the only light incident on the sample imaging region comes from the LED. This provides a means for controlling the light source and obtaining consistent results.

In another embodiment, the container 110 may be integrated with the calibration unit 100 instead of providing separate units as shown in FIG. 1. In this case, the container need not be inserted into a channel of the calibration unit, but may rest on a shoulder or elevated base, as long as the sample imaging region 204 is adequately provided and located with respect to the location marker.

As mentioned above, in addition to the primary embodiment in which the calibration unit 100 is used as a base into which the container is inserted as shown in FIG. 2a, the calibration unit may in the alternative be used as a cap that is placed over the container as shown in FIG. 2b. In this embodiment, the calibration strip 202 will likely be affixed to the calibration unit 100 so that it may be viewed by the user in the appropriate manner, although the smartphone may image the calibration strip 102 regardless of its orientation.

In another embodiment, it may not be necessary to use an imaging background or a container for the sample being measured. For example, a material other than a liquid may be measured that does not require a container, such as a sample of soil or a solid object. In that case, the sample would only need to rest on a platform in the vicinity of the calibration strip, such as on a platform provided instead of the container. In this embodiment, it may not be necessary to utilize the imaging background. Thus, a chemical measurement apparatus may be provided with a calibration unit having a calibration strip extending along a front portion of the calibration unit. The calibration strip includes a location marker and a plurality of calibration indicia juxtaposed in relation to the location marker, wherein each of the plurality of calibration indicia has a different color. A sample of the material is placed in close proximity to the calibration strip so as to form a sample imaging region. A computing device captures an image including the location marker, the plurality of calibration indicia, and the sample imaging region. The processing steps are then performed as described above in order to calibrate the non-standardized color values and generate the calibration model, and then apply the calibration model to the sample color vector to generate a calibrated sample color vector and analyze that calibrated sample color vector with respect to a chemical characteristic model to determine the measurement of the chemical characteristic of the material.

In a further embodiment, a test tube cap may be adapted to provide a stem that extends into the water sample, with a small imaging background attached to the end of the stem such that the imaging background is submerged within the water sample. With this submerged imaging background juxtaposed in the vicinity of the calibration strip as described above, the imaging, calibration, and measurement steps disclosed herein may also be performed.

While the above is a complete description of selected embodiments, it is possible to use various alternatives, modifications, combinations and equivalents. In general, in the following claims, the terms used should be construed to include all possible embodiments along with the full scope of equivalents to which such claims are entitled. Accordingly, the claims are not limited by the disclosure.

What is claimed is:

1. A method for measuring a chemical characteristic of a material comprising:
    providing a chemical measurement apparatus comprising, in combination, a calibration unit and a container comprising a sample of the material, the calibration unit comprising
        a front portion and an imaging background positioned behind the container and viewable through the container and the sample of the material contained therein, wherein a portion of the sample of the material is positioned in front of the imaging background so as to form a sample imaging region, and
        a calibration strip extending along the front portion, the calibration strip comprising a location marker and a plurality of calibration indicia juxtaposed in relation to the location marker, each of the plurality of calibration indicia having a different color;
    capturing, with a computing device, an image comprising the location marker, the plurality of calibration indicia, and the sample imaging region;
    performing a calibration step comprising:
        analyzing the image to determine the location of the location marker within the image,
        calculating, by referencing the location of the location marker, the location within the image of each of the plurality of calibration indicia,
        extracting a non-standardized color value from each of the plurality of the calibration indicia,
        comparing each of the extracted non-standardized color values to previously stored standardized color values for a corresponding calibration indicia, and
        generating a calibration model as a function of comparing the extracted non-standardized color values to the previously stored standardized color values;
    analyzing the sample imaging region from the image to extract a sample color vector;
    applying the calibration model to the sample color vector to generate a calibrated sample color vector; and
    analyzing, with respect to a chemical characteristic model, the calibrated sample color vector to determine the measurement of the chemical characteristic of the material.

2. The method of claim 1 wherein the location marker comprises a first location target and a second location target, and further wherein the plurality of calibration indicia are located in a region between the first location target and the second location target.

3. The method of claim 1, wherein the plurality of calibration indicia comprises a first calibration indicia having a first color, a second calibration indicia having a second color, and a third calibration indicia having a third color.

4. The method of claim 3, wherein the first color is green, the second color is blue, and the third color is red.

5. The method of claim 1 wherein the step of extracting a non-standardized color value from each of the plurality of the calibration indicia further comprises extracting a non-standardized color value from the location marker.

6. The method of claim 1, wherein the calibration unit and the container are an integrated combination.

7. The method of claim 1, wherein the calibration unit and the container are separate units.

8. The method of claim 1 wherein the computing device is a smartphone.

9. The method of claim 1 wherein the chemical measurement apparatus further comprises a coded region juxtaposed in relation to the location marker, the coded region encoded with a printer identification, and wherein the calibration step further comprises
    calculating, by referencing the location of the location marker, the location within the image of the coded region,
    decoding the coded region to provide the printer identification,
    retrieving a printer calibration model associated with the printer identification, and
    adjusting the calibration model as a function of the printer calibration model.

10. The method of claim 9 wherein the coded region is located on the calibration strip.

11. The method of claim 9 wherein the coded region is located on a calibration cap adapted to cover the container.

12. The method of claim 11 wherein the location marker comprises a plurality of location targets, and wherein one of said location targets is located on the calibration cap.

13. The method of claim 1 further comprising
    the computing device receiving a manual input that identifies the chemical characteristic being measured, and
    retrieving the chemical characteristic model as a function of the identification of the chemical characteristic being measured.

14. The method of claim 1 wherein the chemical measurement apparatus further comprises a coded region juxtaposed in relation to the location marker, the coded region encoded with a chemical identification, and wherein the calibration step further comprises
    calculating, by referencing the location of the location marker, the location within the image of the coded region,
    decoding the coded region to provide the chemical identification, and
    retrieving the chemical characteristic model as a function of the identification of the chemical characteristic being measured.

15. The method of claim 14 wherein the coded region is located on the calibration strip.

16. The method of claim 14 wherein the coded region is located on a calibration cap adapted to cover the container.

17. The method of claim 16 wherein the location marker comprises a plurality of location targets, and wherein one of said location targets is located on the calibration cap.

18. A chemical measurement apparatus for measuring a chemical characteristic of a sample of a material in a container, the apparatus comprising:
    a calibration unit comprising:
        a front portion and a rear portion configured to hold the container, and
        an imaging background extending along the rear portion so as to be positioned behind the container when mated with the calibration unit and viewable through the container and the sample of the material contained therein, wherein a portion of the sample of the material is positioned in front of the imaging background so as to form a sample imaging region, and a calibration strip extending along the front portion, the calibration strip comprising a location marker and a plurality of calibration indicia juxtaposed in relation to the location marker, each of the plurality of calibration indicia having a different color; and a computing device comprising image capture means for capturing an image comprising the location marker, the plurality of calibration indicia, and the sample imaging region, memory means for storing the image, and processing means programmed to perform a calibration step comprising analyzing the image to determine the location of the location marker within the image, calculating, by referencing the location of the location marker, the location within the image of each of the plurality of calibration indicia, extracting a non-standardized color value from each of the plurality of the calibration indicia, comparing each of the extracted non-standardized color values to previously stored standardized color values for a corresponding calibration indicia, and generating a calibration model as a function of comparing the extracted non-standardized color values to the previously stored color standard;

analyze the sample imaging region from the image to extract a sample color vector;

apply the calibration model to the sample color vector to generate a calibrated sample color vector; and analyze, with respect to a chemical characteristic model, the calibrated sample color vector to determine the measurement of the chemical characteristic of the material.

19. The chemical measurement apparatus of claim 18 wherein the location marker comprises a first marker indicia and a second marker indicia, and further wherein the plurality of calibration indicia are located in a region between the first marker indicia and the second marker indicia.

20. The chemical measurement apparatus of claim 18, wherein the plurality of calibration indicia comprises a first calibration indicia having a first color, a second calibration indicia having a second color, and a third calibration indicia having a third color.

21. The chemical measurement apparatus of claim 20, wherein the first color is green, the second color is blue, and the third color is red.

22. The chemical measurement apparatus of claim 18 wherein the processing means is further programmed to extract a non-standardized color value from the location marker.

23. The chemical measurement apparatus of claim 18 further comprising the container, wherein the calibration unit and the container are an integrated combination.

24. The chemical measurement apparatus of claim 18 further comprising the container, wherein the calibration unit and the container are separate units.

25. The chemical measurement apparatus of claim 18 wherein the computing device is a smartphone.

26. The chemical measurement apparatus of claim 18 further comprising a coded region juxtaposed in relation to the location marker, the coded region encoded with a printer identification, and wherein the processing means is further programmed to calculate, by referencing the location of the location marker, the location within the image of the coded region, decode the coded region to provide the printer identification, retrieve a printer calibration model associated with the printer identification, and adjust the calibration model as a function of the printer calibration model.

27. The chemical measurement apparatus of claim 26 wherein the coded region is located on the calibration strip.

28. The chemical measurement apparatus of claim 26 further comprising a calibration cap adapted to cover the container, and wherein the coded region is located on the calibration cap.

29. The chemical measurement apparatus of claim 28 wherein the location marker comprises a plurality of location targets, and wherein one of said location targets is located on the calibration cap.

30. The chemical measurement apparatus of claim 18 wherein the processing means is further programmed to receive a manual input that identifies the chemical characteristic being measured, and retrieve the chemical characteristic model as a function of the identification of the chemical characteristic being measured.

31. The chemical measurement apparatus of claim 18 further comprising a coded region juxtaposed in relation to the location marker, the coded region encoded with a chemical identification, and wherein the processing means is further programmed to calculate, by referencing the location of the location marker, the location within the image of the coded region, decode the coded region to provide the chemical identification, and retrieve the chemical characteristic model as a function of the identification of the chemical characteristic being measured.

32. The chemical measurement apparatus of claim 31 wherein the coded region is located on the calibration strip.

33. The chemical measurement apparatus of claim 31 further comprising a calibration cap adapted to cover the container, and wherein the coded region is located on the calibration cap.

34. The chemical measurement apparatus of claim 33 wherein the location marker comprises a plurality of location targets, and wherein one of said location targets is located on the calibration cap.

35. An apparatus comprising a calibration unit for use in measuring a chemical characteristic of a sample of a material in a container, the calibration unit comprising:

a front portion and a rear portion configured to hold the container, and an imaging background extending along the rear portion so as to be positioned behind the container when mated with the calibration unit and viewable through the container and the sample of the material contained therein, wherein a portion of the sample of the material is positioned in front of the imaging background so as to form a sample imaging region, and a calibration strip extending along the front portion, the calibration strip comprising a location marker and a plurality of calibration indicia juxtaposed in relation to the location marker, each of the plurality of calibration indicia having a different color.

36. The apparatus of claim 35 wherein the location marker comprises a first marker indicia and a second marker indicia, and further wherein the plurality of calibration indicia are located in a region between the first marker indicia and the second marker indicia.

37. The apparatus of claim 35 wherein the plurality of calibration indicia comprises a first calibration indicia having a first color, a second calibration indicia having a second color, and a third calibration indicia having a third color.

38. The apparatus of claim 37 wherein the first color is green, the second color is blue, and the third color is red.

39. The apparatus of claim 35 further comprising the container, wherein the calibration unit and the container are an integrated combination.

40. The apparatus of claim 35 further comprising a coded region juxtaposed in relation to the location marker, the coded region encoded with a printer identification.

41. The apparatus of claim 40 wherein the coded region is located on the calibration strip.

42. The apparatus of claim 40 further comprising a calibration cap adapted to cover the container, and wherein the coded region is located on the calibration cap.

43. The apparatus of claim 42 wherein the location marker comprises a plurality of location targets, and wherein one of said location targets is located on the calibration cap.

44. The apparatus of claim 35 further comprising a coded region juxtaposed in relation to the location marker, the coded region encoded with a chemical identification.

45. The apparatus of claim 44 wherein the coded region is located on the calibration strip.

46. The apparatus of claim 44 further comprising a calibration cap adapted to cover the container, and wherein the coded region is located on the calibration cap.

47. The apparatus of claim 46 wherein the location marker comprises a plurality of location targets, and wherein one of said location targets is located on the calibration cap.

* * * * *